(12) United States Patent
Slishman

(10) Patent No.: US 6,413,241 B1
(45) Date of Patent: Jul. 2, 2002

(54) PER KILO DOSER

(75) Inventor: Samuel Slishman, Albuquerque, NM (US)

(73) Assignee: Science & Technology Corporation @UNM, Albuquerque, NM (US)

(*) Notice: Subject to any disclaimer, the term of this patent is extended or adjusted under 35 U.S.C. 154(b) by 0 days.

(21) Appl. No.: 09/541,023

(22) Filed: Mar. 31, 2000

(51) Int. Cl.[7] .............................................. A61M 5/178
(52) U.S. Cl. ...................................................... 604/186
(58) Field of Search ................................ 604/408, 186, 604/185, 181, 207, 212, 217, 298; 73/864, 864.11

(56) References Cited

U.S. PATENT DOCUMENTS

| | | | |
|---|---|---|---|
| 3,391,694 A | * | 7/1968 | Spaeth |
| 3,437,243 A | | 4/1969 | Farnsworth |
| 4,085,866 A | | 4/1978 | Fekl |
| 4,561,110 A | * | 12/1985 | Herbert ...................... 604/408 |
| RE32,065 E | * | 1/1986 | Ralston, Jr. et al. ........ 604/408 |
| 5,154,702 A | * | 10/1992 | Foyil |
| 5,259,843 A | * | 11/1993 | Watanabe et al. ........... 604/256 |
| 5,502,056 A | * | 3/1996 | Breitbarth |
| 5,545,144 A | | 8/1996 | Fryklund et al. |
| 5,601,605 A | * | 2/1997 | Crowe et al. |
| 5,875,931 A | * | 3/1999 | Py |
| 5,876,380 A | | 3/1999 | Manganini et al. |
| 5,932,206 A | * | 8/1999 | Pine et al. |
| 5,947,934 A | | 9/1999 | Hansen et al. |

OTHER PUBLICATIONS

Infant's Motrin concentrated Drops Instructions.*
Application Ser. No. 2001/0048898 (Buehler); Application Ser. No. 2001/0049391 (Alfonso et al.); Application Ser. No. 2001/0042572 (Faughey et al.); and Application Ser. No. 2001/0027301 (Lau et al.).*

* cited by examiner

*Primary Examiner*—Manuel Mendez
(74) *Attorney, Agent, or Firm*—Jagtiani & Guttag

(57) ABSTRACT

The present invention provides a syringe comprising a syringe barrel having a plurality of non-volumetric measuring indicia thereon. The present invention also provides a container comprising: at least one chamber; a plurality of non-volumetric measuring indicia on the at least one chamber; and an opening control device in the at least one chamber for allowing liquid contained in the at least one chamber to be withdrawn from the at least one chamber.

20 Claims, 8 Drawing Sheets

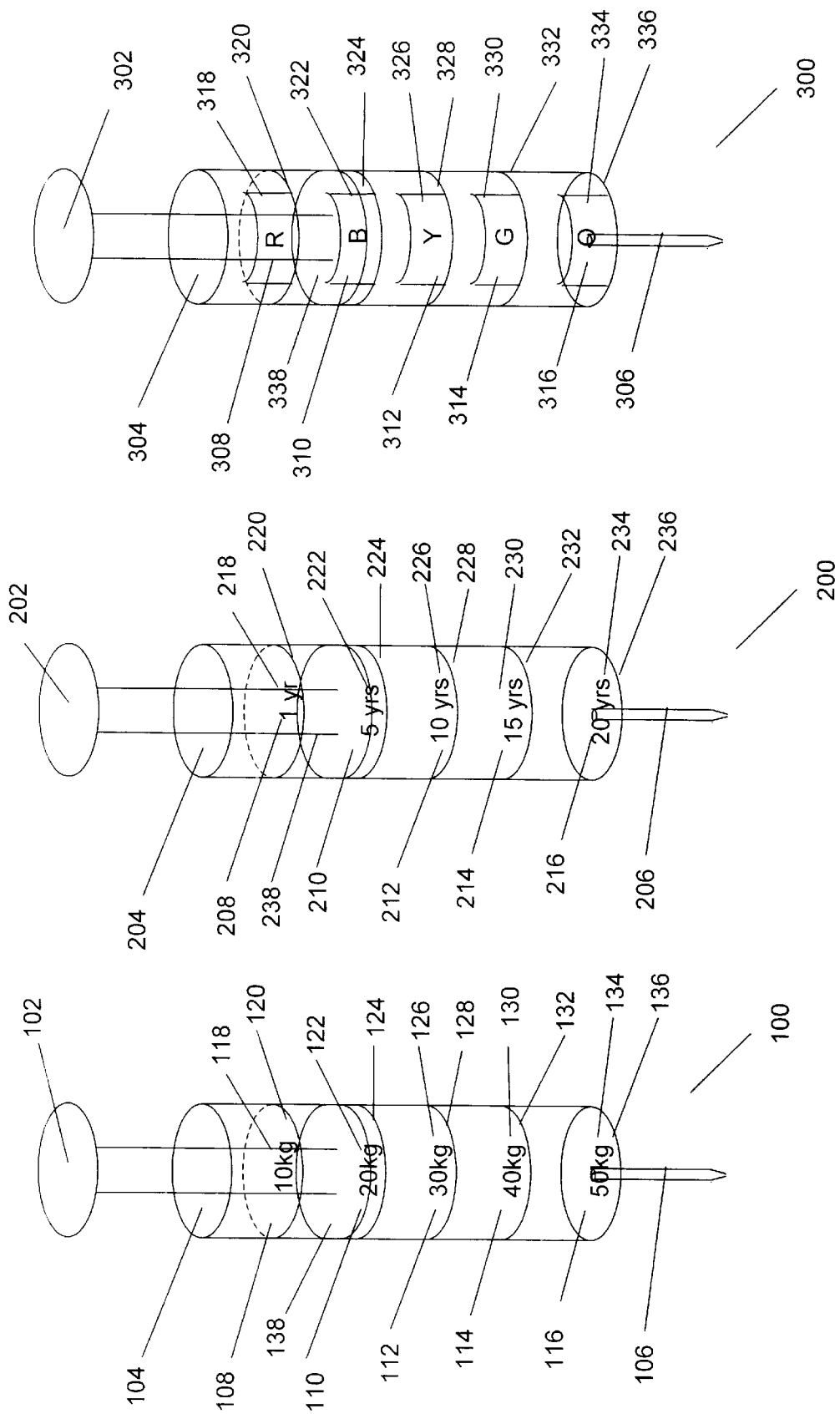

PER KILO DOSER

BACKGROUND OF THE INVENTION

1. Field of the Invention

The present invention relates generally to syringes and containers for measured dosages of a liquid medication.

2. Description of the Prior Art

The terms "medication error", "adverse drug reaction", and "adverse drug event are used frequently in the literature and have different meanings. The National Coordinating Council for Medication Error Reporting and Prevention defines medication error as "any preventable event that may cause or lead to inappropriate medication use or patient harm while the medication is in the control of the health care professional, patient or consumer. Such events may be related to professional practice, health care products, procedures, and systems including prescribing; prescribing, order communication; product labeling; packaging; and nomenclature; compounding; dispensing; distribution; administration; education; monitoring; and use.

The World Health Organization defines an Adverse Drug Reaction (ADR) as "any noxious, unintended, and undesired, effect of a drug which occurs at doses used in humans for prophylaxis, diagnosis, or therapy." This definition excludes among other things, adverse events due to errors in drug administration or non-compliance (taking more or less of a drug than the prescribed amount. The term Adverse Drug Event (ADE) is also used and unlike the ADR definition, does include errors in administration.

Several studies have demonstrated the high incidence of medication errors and the sometimes fatal results. For example, a Harvard Medical Practice Study surveyed 30,000 hospitalizations in several New York hospitals and found 3.7% of the patients experienced serious, disabling medical injuries, with 45% of them due to errors, see Leape, L., et al., "Systems Analysis of Adverse Drug Events," *Journal of the American Medical Association*, Jul. 5, 1995, Vol. 274, No.1, pp.35–43. Also, a death certificate study found a greater than two-fold increase in deaths caused by medication errors between 1993, during which 7,391 people died, and 1983, when 2,876 patients died from medication errors, see Phillips, D. P., et al., "Increase in U.S. Medication-Error Deaths Between 1983 and 1993," *The Lancet*, Feb. 28, 1998, Vol. 351, No. 9103. Another report estimates that 6.5 ADE's per 100 admissions, as well as an additional cost of $2,000 per adverse drug event for a hospitalized patient, excluding malpractice costs or cost of injury to the patient. Furthermore, while most ADE's are a result of errors at the ordering stage, many occurred at the administering stage, as estimated by the study, see Bates, D. W., et al., "Incidence of Adverse Drug Events and Potential Adverse Drug Events," *Journal of the American Medical Association*, Jul. 5, 1995, Vol. 274, No. 1, pp. 29–30. In addition, in large analysis insurance claims, injuries due to drugs were the most frequent cause of a procedure-related malpractice claim, see Leap, et al., 1995, *JAMA*, supra, and accounted for the highest total of expenditures of any type of procedure-related injury, see Bates, et al., 1995, *JAMA*, supra. A study by Lazarou, et al. study found between 76,000 and 106,000 deaths were caused by ADR's, see Lazarou, J. et al., "Incidence of adverse Drug Reactions in Hospitalized Patients", *JAMA*, Apr. 15, 1998, Vol. 279, no. 15, pp. 1200–1205.

From a pediatric standpoint, a four-year study that investigated patterns of medication errors in neonatal and pediatric intensive care-units is instructive. Researchers found an error rate of 14.7% with one medication error occurring for every 6.8 admissions. The study found that while the percentage breakdown varied, all health care providers: physicians, nurses, and pharmacists, were responsible, see Raju TNK, et al., "Medication Errors in neonatal and pediatric intensive care units," *The Lancet*, 1989, August. 12, pp. 374–376.

A 1993 study form the University of Wales clearly illustrates the complexity physicians face and the potential for medication error. Resident pediatrician's pediatric advanced knowledge was evaluated following participation in a rigorous training program. The results reflected the difficulty faced by health care practitioners: only 52% could provide the correct dosage of epinephrine to be administered to a child during cardiac arrest, without using a reference text, see Buss, PW, et al., "A Survey of basic resuscitation knowledge among resident pediatricians," *Archive of Disease in Childhood*, 1993, 68:75–8.

Human error is also not limited to physicians. A test administered to 100 registered nurses that assessed only mathematical calculating ability and involved questions concerning oral, intramuscular, and intravenous drugs yielded similar distressing results. The mean error rate was 19% on intramuscular/subcutaneous calculation questions, 36% on oral medication and 48% for intravenous drug delivery, see Bindler, et al., "Medication calculation ability of registered nurses," *Image: Journal of Nursing Scholarship*, 1991, 23:331–224.

Medication errors include dose miscalculation, improper dosage delivery, and accidental administration of the wrong drug. While hospitals have voluntary reporting system in place, research has shown them to be inaccurate. A study of a voluntary system that uncovered only one medication errors per 1,000 drug orders, revealed an actual error rate of 32 per 1,000 medication errors, see Anderson, J. G., et al., "Evaluating the Potential Effectiveness of Using Computerized Information Systems to Prevent Adverse Drug Events," *AMIA*, Inc., 1997, pp. 228–232. The cost of ADR's and ADE's is tremendous. While Anderson, et al. estimates that ADE's annually result in 1,400 to 4,656 days of extra hospitalization with excess hospital costs ranging from $1.6 million to $5.5 million, U.S. Pharmacopoeia (USP) calculates ADE's cost approximately $400 million per year in the U.S., excluding malpractice costs or cost of injury to the patient.

One attempt to reduce ADR's and ADE's has been to use prefilled syringes to avoid the risk of misidentification, and contamination. However, using a prefilled syringe still requires a physician or nurse to perform a mathematical calculation to convert between a patient's height or weight to the volume of drug to be administered. In addition, using prefilled syringes necessitates having separate syringes for each drug that may be administered to a patient. Furthermore, for storing a given volume of a liquid medication, prefilled syringes are both awkward to store and require a great deal of space to store, when compared storing a liquid medication in one or more vials.

SUMMARY OF THE INVENTION

It is therefore an object of the present invention to provide a drug delivery system that reduces the possibility of adverse drug events.

It is another object of the present invention to provide a drug delivery system that avoids the need to perform a mathematical calculation to determine the amount of medication to be administered to an individual.

It is yet another object o the present invention to provide a drug delivery system that may be used to administer a number of medications quickly and easily.

It is yet another object of the present invention to provide a drug delivery system that may be used with existing vials for drugs.

According to a first broad aspect, the present invention provides syringe comprising a syringe barrel having a plurality of non-volumetric measuring indicia thereon.

According to a broad second aspect, the present invention provides a container comprising: at least one chamber; a plurality of non-volumetric measuring indicia on the at least one chamber; and an opening control device in the at least one chamber for allowing liquid contained in the at least one chamber to be withdrawn from the at least one chamber.

Other objects and features of the present invention will be apparent from the following detailed description of the preferred embodiment.

BRIEF DESCRIPTION OF THE DRAWINGS

The invention will be described in conjunction with the accompanying drawings, in which:

FIG. 1 is an illustration in simplified form of a syringe made according to the present invention;

FIG. 2 is an illustration in simplified form of another syringe made according to the present invention;

FIG. 3 is an illustration in simplified form of another syringe made according to the present invention;

DETAILED DESCRIPTION OF THE PREFERRED EMBODIMENT

Figure 4:
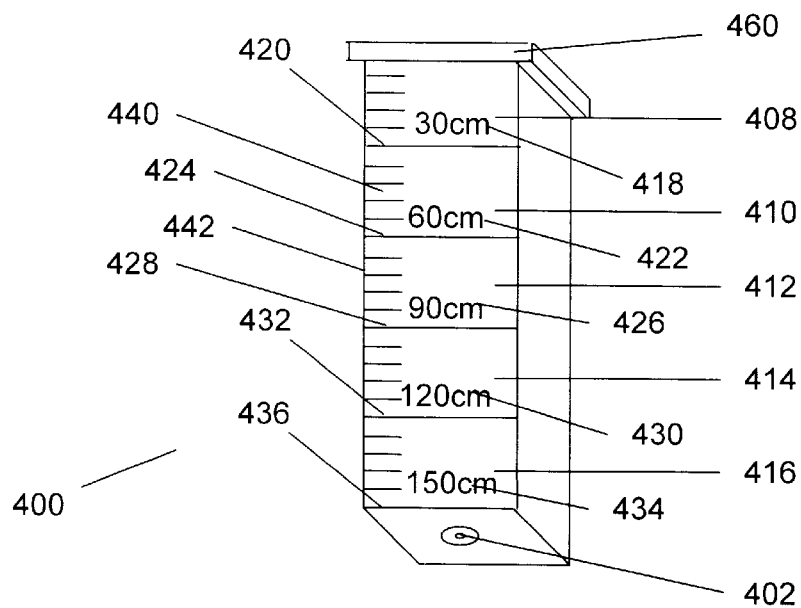
FIG. 4 is an illustration in simplified form of a container made according to the present invention.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "volumetric measuring indicia" refers to numbers indicating amount of liquid in a syringe or container in terms of the liquid's volume.

For the purposes of the present invention, the term a "non-volumetric measuring indicia" refers to numbers, characters, colored markers or other indicia on a syringe or container that are not merely representative of the volume of a liquid contained in the syringe or container. One example of "non-volumetric measuring indicia" is a series of numbers on a syringe that indicate the amount of liquid that should be administered to an individual based on the individual's age height, or weight. Another example of non-volumetric measuring indicia is a series of colored marks on a container that indicate the proper dosage of a liquid to be administered to an individual, based on the individual's weight or age. For example, a red mark could indicate the dose for a 1 year old, a blue mark the dose for a 5 year old, a yellow mark the dose for a 10 year old, etc. Yet another example of non-volumetric measuring indicia would be pictorial indicia, such as a picture depicting a baby for one dosage, a picture depicting a child for a second dosage, and a picture depicting an adult for a third dosage. The non-volumetric indicia of the present invention may include other markings, such as lines, used with conventional volumetric measuring indicia. For example, a non-volumetric measuring indicia of the present invention could comprise the characters "20 kg" and a line below the characters "20 kg" marked on a syringe of the present invention. The line below the characters would indicate the level of liquid medication that must be dispensed by the syringe to administer a dosage for an individual weighing up to 20 kg. Yet another example of non-volumetric measuring indicia covered by the present invention is to make sections of a syringe or a container of the present invention different translucent colors. In such an embodiment, the translucent colors may correspond to particular weights, ages, etc. of individuals. The fact that the colors are translucent would allow the level of liquid medication in the syringe or container to be determined.

For the purposes of the present invention, the term "primary non-volumetric measuring indicia" refers to non-volume measuring indicia between which there are one or more "secondary non-volumetric measuring indicia". For the purposes of the present invention, the term "indicia" refers to both an individual indicium as well as multiple indicia. The secondary non-volumetric measuring indicia indicates amounts of fluid intermediate between the amounts indicated by the primary non-volumetric measuring indicia, or between primary non-volumetric measuring indicia and an end of a container or a syringe of the present invention. Although for simplicity, primary and secondary non-volumetric measuring indicia are only shown for a few of the syringes and containers of the present invention described below and shown in the drawing figures, primary and second non-volumetric measuring indicia may be used with various syringes and containers, of different sizes and shapes, of the present invention.

For the purposes of the present invention, the term "individual" refers to either an individual person or animal.

For the purposes of the present invention, the term "opening control device" refers to any device that controls or limits the ability of liquid to be withdrawn from a container of the present invention. When a syringe needle is used to withdraw liquid from a container of the present invention, the opening control device may be a sealed opening, a conventional resealable opening for receiving a syringe such as an opening with a valve for opening and closing the opening, etc. The opening control device may even be as simple as a wall of the container that is thin enough for a syringe needle to penetrate and withdraw liquid from the container. The opening control device may also take the form of a valve, such as a conventional luer lock valve or adapter that allows a luer or tube to be attached to the container and liquid to be withdrawn when the valve is opened.

For the purposes of the present invention, the term "withdrawal device" refers to any device such as a syringe, luer, tube, etc. that may be used to withdraw liquid from a container of the present invention. The term "withdrawal device" also encompasses a valve mounted on a container of the present invention that allows liquid to be withdrawn from the container when the valve is in an open position.

For the purposes of the present invention, the term "drug" or "liquid medication" refers to any type of liquid or solution that is commonly considered a drug or medication. For the purposes of the present invention, a drug may be a substance that acts on the central nervous system of an individual, e.g. a narcotic, hallucinogen, barbiturate, or a psychotropic drug. For the purposes of the present invention, a drug may also be a substance that kills or inactivates disease-causing infectious organisms. In addition, for the purposes of the present invention, a drug may be a substance that affects the activity of a specific cell, bodily organ, or function. A drug may be an organic or inorganic chemical, a biomaterial, etc.

For the purposes of the present invention, the term "modular container" refers to a container of the present invention that has chambers that may be attached or detached from the container.

Description

FIG. 1 illustrates a syringe 100 of the present invention. Syringe 100 includes a plunger 102, a syringe barrel 104 and a needle 106. On the outside of syringe barrel 104 are non-volumetric measuring indicia 108, 110, 112, 114, and 116 that correspond to dosages based on an individual's weight. Non-volumetric measuring indicia 108, comprising characters 118 and line 120, corresponds to the dosage for an individual weighing 0 to 10 kg. Non-volumetric measuring indicia 110, comprising characters 122 and line 124, corresponds to the dosage for an individual weighing 10 to 20 kg. Non-volumetric measuring indicia 112, comprising characters 126 and line 128, corresponds to the dosage for an individual weighing 20 to 30 kg. Non-volumetric measuring indicia 114, comprising characters 130 and line 132, corresponds to the dosage for an individual weighing 30 to 40 kg. Non-volumetric measuring indicia 116, comprising characters 134 and line 136, corresponds to the dosage for an individual weighing 40 to 50 kg. A stopper 138 of plunger 110 has been pushed into syringe barrel 104 to force out through needle 106 into an individual (not shown) a dosage of a liquid medication (not shown) sufficient for an individual weighing between 10 and 20 kg.

FIG. 2 illustrates a syringe 200 of the present invention. Syringe 200 includes a plunger 202, a syringe barrel 204 and a needle 206. On the outside of syringe barrel 204 are non-volumetric measuring indicia 208, 210, 212, 214, and 216 that correspond to dosages based on an individuals age. Non-volumetric measuring indicia 208, comprising characters 218 and line 220, corresponds to the dosage for an individual of up to 1 year of age. Non-volumetric measuring indicia 210, comprising characters 222 and line 224, corresponds to the dosage for an individual of 1 to 5 years of age. Non-volumetric measuring indicia 212, comprising characters 226 and line 228, corresponds to the dosage for an individual of 5 to 10 years of age. Non-volumetric measuring indicia 214, comprising characters 230 and line 232, corresponds to the dosage for an individual of 10 to 15 years of age. Non-volumetric measuring indicia 216, comprising characters 234 and line 236, corresponds to the dosage for an individual of 15 to 20 years of age. A stopper 238 of plunger 210 has been pushed into syringe barrel 204 to force out through needle 206 into an individual (not shown) a dosage of a liquid medication (not shown) sufficient for an individual who is between 1 and 5 years old.

FIG. 3 illustrates a syringe 300 of the present invention. Syringe 300 includes a plunger 302, a syringe barrel 304, and a needle 306. On the outside of syringe barrel 304 are non-volumetric measuring indicia 308, 310, 312, 314, and 316 that correspond to dosages based on an individual's height. Non-volumetric measuring indicia 308, comprises a red marking 318, indicated by the letter R, and a line 320. Non-volumetric measuring indicia 308 corresponds to the dosage for an individual 0 to 30 cm tall. Non-volumetric measuring indicia 310 comprises a blue marking 322, indicated by the letter B, and a line 324. Non-volumetric measuring indicia 310 corresponds to the dosage for an individual 30 cm to 60 cm tall. Non-volumetric measuring indicia 312 comprises a yellow marking 326, indicated by the letter Y, and a line 328. Non-volumetric measuring indicia 312 corresponds to the dosage for an individual 60 cm to 90 cm tall. Non-volumetric measuring indicia 314 comprises a green marking 330, indicated by the letter G, and a line 332. Non-volumetric measuring indicia 314 corresponds to the dosage for an individual 90 cm to 120 cm tall. Non-volumetric measuring indicia 316 comprises a purple marking 334, indicated by the letter P, and a line 336. Non-volumetric measuring indicia 334 corresponds to the dosage for an individual 120 cm to 150 cm tall. A stopper 338 of plunger 310 has been pushed into syringe barrel 304 to force out through needle 306 into an individual (not shown) a dosage of a liquid medication (not shown) sufficient for an individual weighing between 30 cm and 60 cm tall.

The syringe of the present invention may be made of any conventional material used for making syringes, such as transparent or translucent plastic. The syringe of the present invention may also be of any size, shape or structure conventionally used for syringes.

FIG. 4 illustrates a container 400 of the present invention. Container 400 includes a resealable opening 402 into which a syringe (not shown) may be inserted. Resealable opening 402 is a conventional resealable opening or valve device made of rubber, plastic, cork etc. that is conventionally used to allow a liquid in a container to be withdrawn by a syringe or other withdrawal device. On the outside of container 400 are primary non-volumetric measuring indicia 408, 410, 412, 414, and 416 that correspond to dosages based on an individual's height. Primary non-volumetric measuring indicia 408 comprises characters 418 and a line 420. Primary non-volumetric measuring indicia 408 corresponds to the dosage for an individual 30 cm tall. Primary non-volumetric measuring indicia 410 comprises characters 422 and a line 424. Primary non-volumetric measuring indicia 410 corresponds to the dosage for an individual 60 cm tall. Primary non-volumetric measuring indicia 412 comprises characters 426 and a line 428. Primary non-volumetric measuring indicia 412 corresponds to the dosage for an individual 90 cm tall. Primary non-volumetric measuring indicia 414 comprises characters 430 and a line 432. Primary non-volumetric measuring indicia 414 corresponds to the dosage for an individual 120 cm tall. Primary non-volumetric measuring indicia 416 comprises characters 434 and a line 436. Primary non-volumetric measuring indicia 416 corresponds to the dosage for an individual 150 cm tall. Container 400 also includes secondary non-volumetric measuring lines or indicia 440 between each of primary non-volumetric measuring indicia 408, 410, 412, 414, and 416 to allow dosages to be measured for individuals whose weights do not correspond to one of primary non-volumetric measuring indicia 408, 410, 412, 414, and 416. In use, a syringe or other withdrawal device (not shown) may be inserted into container 400 through resealable opening 402 to withdraw the appropriate amount of a liquid medication (not shown) that fills container 400. For example, to withdraw the proper dosage for an individual 72 cm tall, sufficient liquid medication is drawn into a syringe (not shown) to lower the level of liquid in container 400 to the level of specific indicia 442 of secondary non-volumetric measuring indicia 440. Container 400 may be filled or refilled with a liquid medication (not shown) by removing a cap 460 that snap fits onto container 400. Although only one type of cap is shown in FIG. 4, any kind of conventional cap may be used to close container 400.

Figure 5:
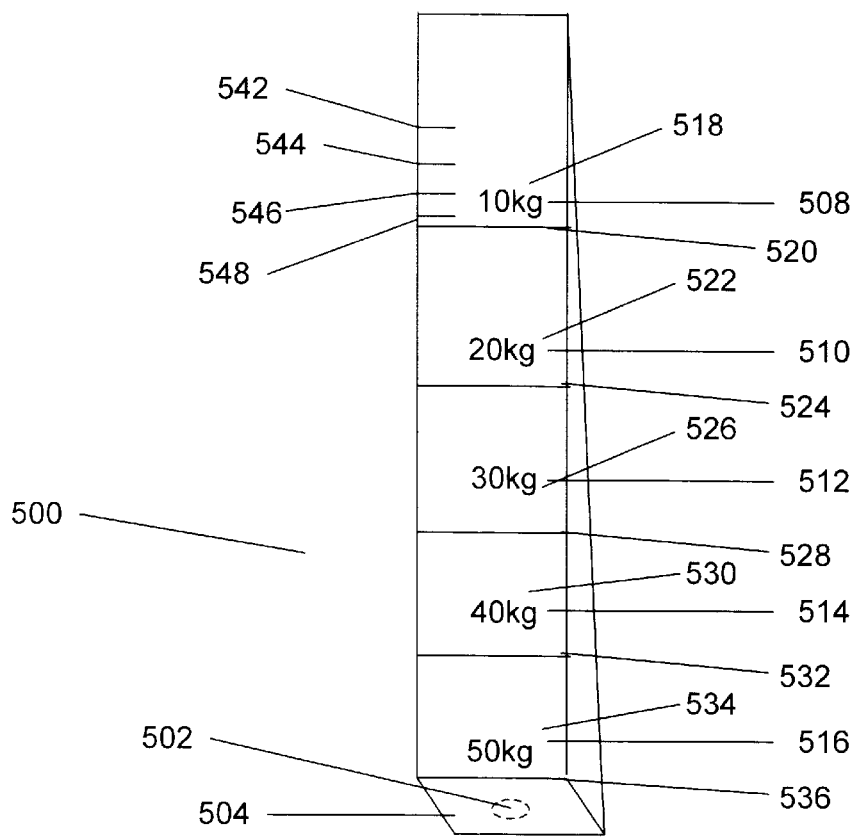
FIG. 5 is an illustration in simplified form of another container made according to the present invention.

FIG. 5 illustrates a container 500 of the present invention having a right triangularly tapered profile. Container 500 includes an opening 502, shown by shadow lines, sealed and covered by a seal 504 comprised of a sealing material. Suitable sealing materials for seal 504 include: a plastic strip, aluminum foil, a piece of tape, etc. In order to withdraw a liquid medication (not shown) from container 500, the needle of the syringe is inserted through sheet 504 through opening 502 into container 500. On the outside of container 500 are primary non-volumetric measuring indicia 508, 510, 512, 514, and 516 that correspond to dosages based on an individual's weight. Primary non-volumetric measuring indicia 508 comprises characters 518 and a line 520. Primary non-volumetric measuring indicia 508 corresponds to the dosage for an individual weighing 0 to 10 kg. Primary non-volumetric measuring indicia 510 comprises characters 522 and a line 524. Primary non-volumetric measuring indicia 510 corresponds to the dosage for an individual weighing 10 to 20 kg. Primary non-volumetric measuring indicia 512 comprises characters 526 and a line 528. Primary non-volumetric measuring indicia 512 corresponds to the dosage for an individual weighing 20 to 30 kg. Primary non-volumetric measuring indicia 514 comprises characters 530 and a line 532. Primary non-volumetric measuring indicia 514 corresponds to the dosage for an individual weighing 30 to 40 kg. Primary non-volumetric measuring indicia 516 comprises characters 534 and a line 536. Primary non-volumetric measuring indicia 516 corresponds to the dosage for an individual weighing 40 to 50 kg. Container 500 also includes secondary non-volumetric measuring indicia 542, 544, 546, and 548. Secondary non-volumetric measuring indicia 542 corresponds to the dosage for an individual weighing 2 kg. Secondary non-volumetric measuring indicia 544 corresponds to the dosage for an individual weighing 4 kg. Secondary non-volumetric measuring indicia 546 corresponds to the dosage for an individual weighing 6 kg. Secondary non-volumetric measuring indicia 548 corresponds to the dosage for an individual weighing 8 kg. In use, a syringe or other withdrawal device (not shown) may be inserted into container 500 through opening 502 to withdraw the appropriate amount of a liquid medication (not shown) that fills container 500. For example, to withdraw the proper dosage for an individual weighing 8 kg, sufficient liquid medication is drawn into a syringe (not shown) to lower the level of liquid in container 500 to the level of secondary non-measuring indicia 548. Because container 500 has a right-triangularly tapered profile, the non-volumetric measuring indicia on container 500, unlike the non-volumetric measuring indicia on the rectangular container shown in FIG. 4, are not evenly spaced from each other. As container 500 narrows in profile towards the top of container 500, the amount of liquid contained in a given distance up the container decreases. Using a container having such a triangular profile can be particularly valuable when dosages must be measured for small children where slight differences in the unit dosage amount result in higher percentage bodyweight changes in dosage and may be critical to effective care of an individual receiving such dosages. Before sealing opening 502 with seal 504, container 500 may be filled with a liquid medication through opening 502.

Figure 6A:
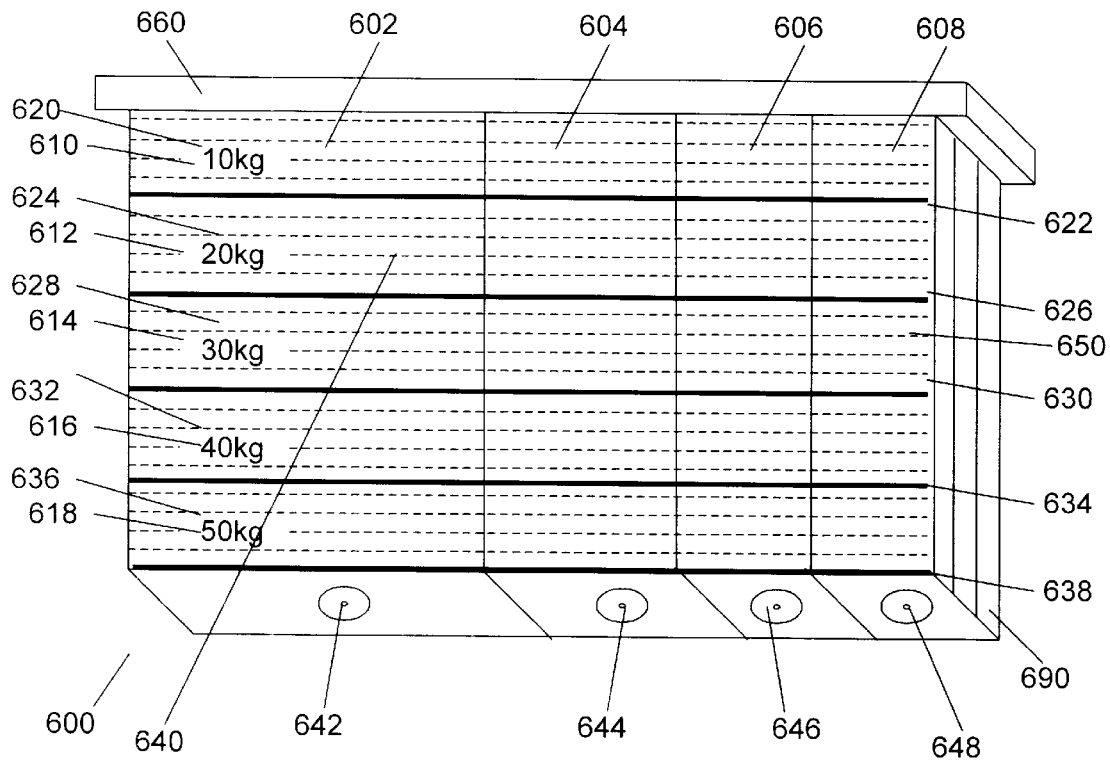
FIG. 6A is an illustration in simplified form of another container made according to the present invention.
Figure 6B:
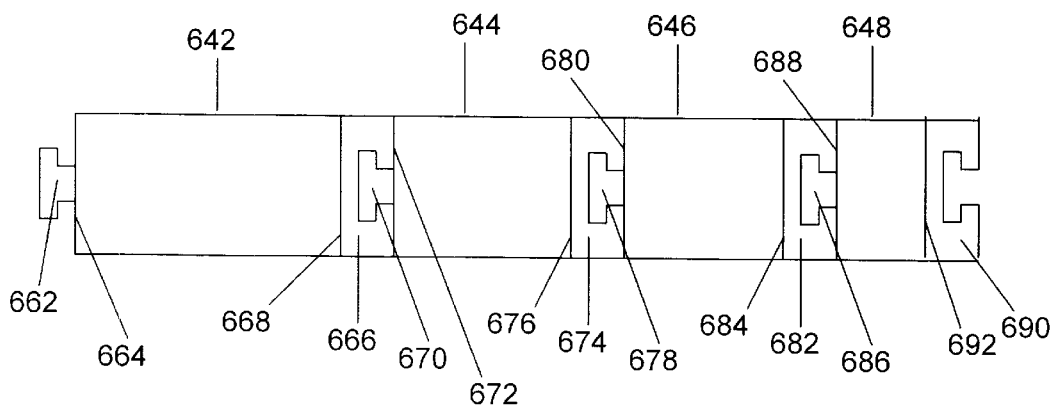
FIG. 6B is a cross-sectional view, in simplified form, of the container of FIG. 6A.

FIGS. 6A and 6B illustrate a multi-chamber container 600 of the present invention having a rectangular profile. Multi-chamber container 600 includes four sub-containers or chambers 602, 604, 606, and 608 for four different liquid medications (not shown). Each of chambers 602, 604, 606, and 608 may be a different size, because the dosage amounts of each of the liquid medications (not shown) may be different for an individual of a given weight. On the outside of multi-chamber container 600 are primary non-volumetric measuring indicia 610, 612, 614, 616 and 618 that correspond to dosages for the liquid medications (not shown) in each of chambers 602, 604, 606, and 608, based on an individual's weight. Primary non-volumetric measuring indicia 610 comprises characters 620 and a line 622. Primary non-volumetric measuring indicia 610 corresponds to the dosages for an individual weighing 10 kg. Primary non-volumetric measuring indicia 612 comprises characters 624 and a line 626. Primary non-volumetric measuring indicia 612 corresponds to the dosages for an individual weighing 20 kg. Primary non-volumetric measuring indicia 614 comprises characters 628 and a line 630. Primary non-volumetric measuring indicia 614 corresponds to the dosages for an individual weighing 30 kg. Primary non-volumetric measuring indicia 616 comprises characters 632 and a line 634. Primary non-volumetric measuring indicia 616 corresponds to the dosages for an individual weighing 40 kg. Primary non-volumetric measuring indicia 618 comprises characters 636 and a line 638. Primary non-volumetric measuring indicia 618 corresponds to the dosages for an individual weighing 50 kg. Container 600 also includes secondary non-volumetric measuring indicia or lines 640 between each of primary non-volumetric measuring indicia 610, 612, 614, 616, and 618 to allow dosages to be measured for individuals whose weights do not correspond to one of primary non-volumetric measuring indicia 610, 612, 614, 616, and 618. In use, a syringe or other withdrawal device (not shown) may be inserted into multi-chamber container 600 through resealable openings 642, 644, 646, and 648 to withdraw the appropriate amount of each of the four liquid medications in chambers 602, 604, 606, and 608, respectively. Resealable openings 642, 644, 646, and 648 are conventional resealable openings or valve devices made of rubber, plastic, cork etc. that are conventionally used to allow a liquid in a container to be withdrawn by a syringe or other withdrawal device. For example, to withdraw the proper dosages for an individual weighing 24 kg, sufficient liquid medications are drawn into a syringe (not shown) to lower the level of liquid in each of chambers 602, 604, 606, and 608 to the level of specific indicia 650 of secondary non-volumetric measuring indicia 640. Container 600 may be filled or refilled with a liquid medication (not shown) by removing a cap 660 that snap fits onto container 600. Although only one type of cap is shown in FIG. 6A, any kind of conventional cap may be used to close container 600.

As illustrated in FIG. 6B, chamber 602 includes a male sliding connector 662 on a left wall 664, and a female sliding connector 666 on a right wall 668 of chamber 602. Chamber 604 includes a male sliding connector 670 on a left wall 672 and a female sliding connector 674 on a right wall 676 of chamber 604. Chamber 606 includes a male sliding connector 678 on a left wall 680 and a female sliding connector 682 on a right wall 684 of chamber 606. Chamber 608 includes a male sliding connector 686 on a left wall 688 and a female sliding connector 690 on a right wall 692 of chamber 608. Chamber 604 is fitted onto chamber 602 by sliding male sliding connector 670 into female sliding connector 666. Chamber 606 is fitted onto chamber 604 by sliding male sliding connector 678 into female sliding connector 674. Chamber 608 is fitted onto chamber 606 by sliding male sliding connector 686 into female sliding connector 682. Container 600 can be expanded by fitting additional (chambers) not shown having male and female sliding connectors onto container 600. Similarly, container 600 may be reduced by using fewer chambers than shown in FIGS. 6A and 6B.

Although only one type of connector is shown in FIG. 6B to allow for the formation of a modular container, other forms of known modular connectors may be used to form modular containers of the present invention.

Figure 7A:
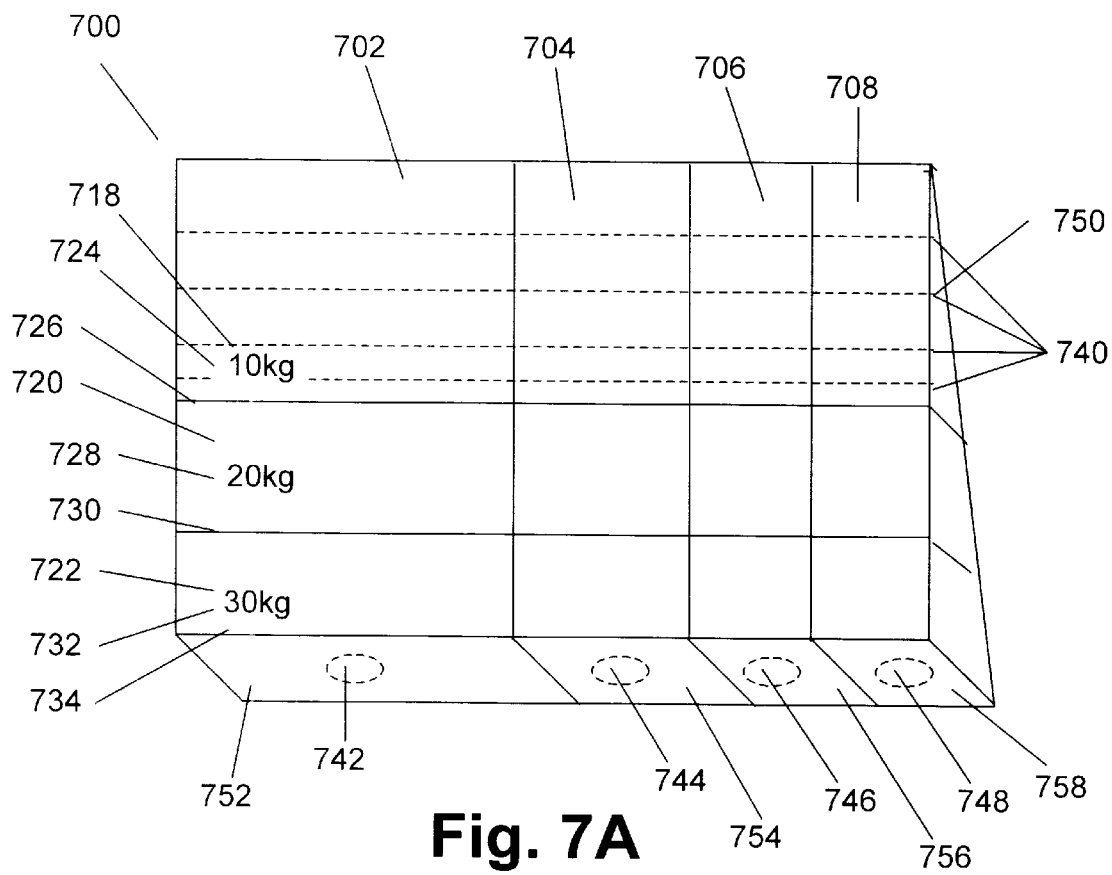
FIG. 7A is an illustration in simplified form of another container made according to the present invention.
Figure 7B:
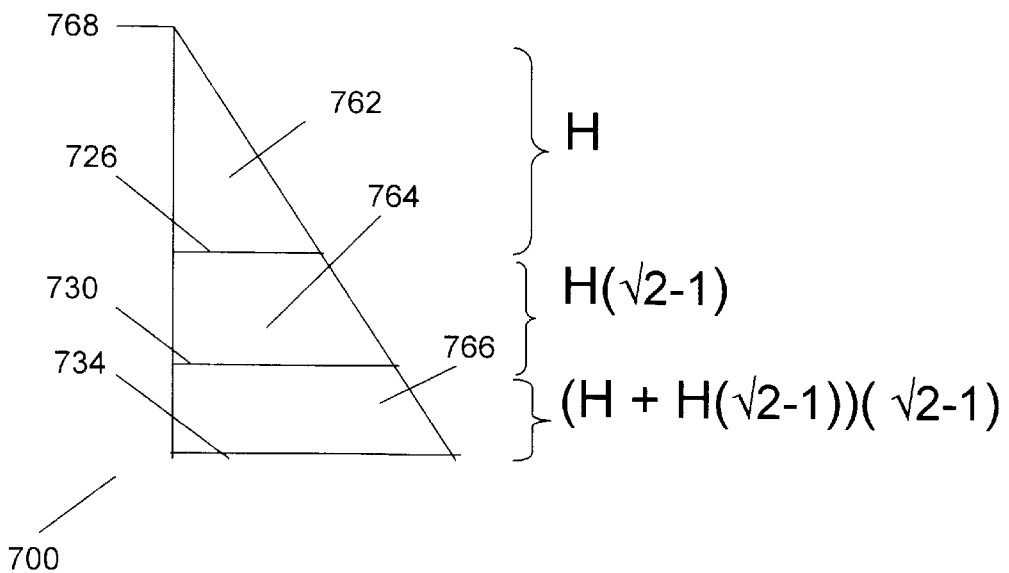
FIG. 7B is a side view of the container of FIG. 7A in simplified form of another container made according to the present invention.

FIGS. 7A and 7B illustrate a multi-chamber container 700 of the present invention having a triangularly tapered profile. Multi-chamber container 700 includes four sub-containers or chambers 702, 704, 706, and 708 for four different liquid medications (not shown). Each of chambers 702, 704, 706, and 708 may be a different size, because the dosage amount of each of the medications may be different for an individual of a given weight. On the outside of multi-chamber container 700 are primary non-volumetric measuring indicia 718, 720, and 722 that correspond to dosages for the liquid medications (not shown) in each of chambers 702, 704, 706, and 708 based on an individual's weight. Primary non-volumetric measuring indicia 718 comprises characters 724 and a line 726. Primary non-volumetric measuring indicia 718 corresponds to the dosages for an individual weighing 10 kg. Primary non-volumetric measuring indicia 720 comprises characters 728 and a line 730. Primary non-volumetric measuring indicia 720 corresponds to the dosages for an individual weighing 20 kg. Primary non-volumetric measuring indicia 722 comprises characters 732 and a line 734. Primary non-volumetric measuring indicia 722 corresponds to the dosages for an individual weighing 30 kg. Container 700 also includes secondary non-volumetric measuring indicia or lines 740 between each of primary non-volumetric measuring indicia 718, 720, and 722 to allow dosages to be measured for individuals whose weights do not correspond to one of primary non-volumetric measuring indicia 718, 720, and 722. In use, a syringe or other withdrawal device (not shown) is inserted into multi-chamber container 700 through sealed openings 742, 744, 746, and 748 (shown by shadow lines) to withdraw the appropriate amount of each of the four liquid medications in chambers 702, 704, 706, and 708, respectively. For example, to withdraw the proper dosages for an individual weighing 4 kg, sufficient liquid medications are drawn into a syringe (not shown) to lower the level of liquid in each of chambers 702, 704, 706, and 708 to the level of specific indicia 750. Openings 742, 744, 746, and 748 are covered and sealed by seals 752, 754, 756, and 758, respectively. Suitable sealing materials for seals 752, 754, 756, and 758 include: plastic strips, aluminum foil, pieces of tape, etc. Before openings 742, 744, 746, and 748 are sealed, liquid medications may be poured, or injected into chambers 702, 704, 706, and 708 through openings 742, 744, 746, and 748, respectively.

FIG. 7B indicates how the distance between primary non-volumetric measuring indicia changes throughout the height of multi-chamber container 700. Because container 700 has a right angular profile, in order to have equal volumes of liquid medication (not shown) in each of sections 762, 764, and 766, the distance between container top 768 and line 726 is H, the distance between line 726 and line 730 is H ($\sqrt{2}-1$), and the distance between line 730 and line 734 is H+H($\sqrt{2}-1$) ($\sqrt{2}-1$).

Figures 8, 9:
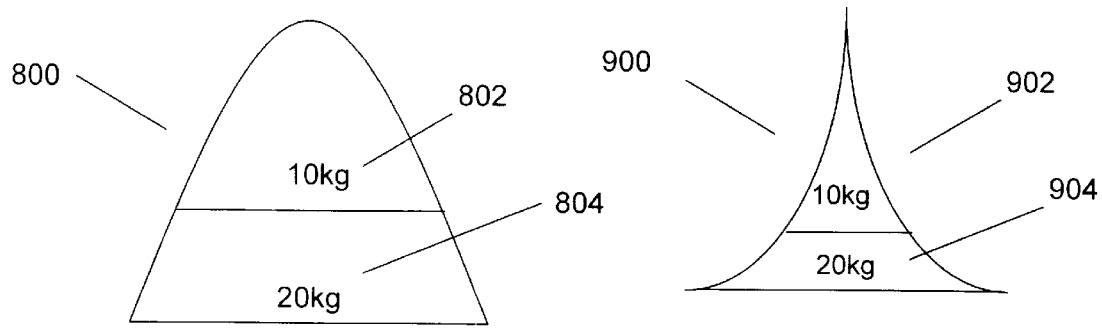
FIG. 8 is an illustration in simplified form of another container made according to the present invention.
FIG. 9 is an illustration in simplified form of another container made according to the present invention.
Figures 10, 11:
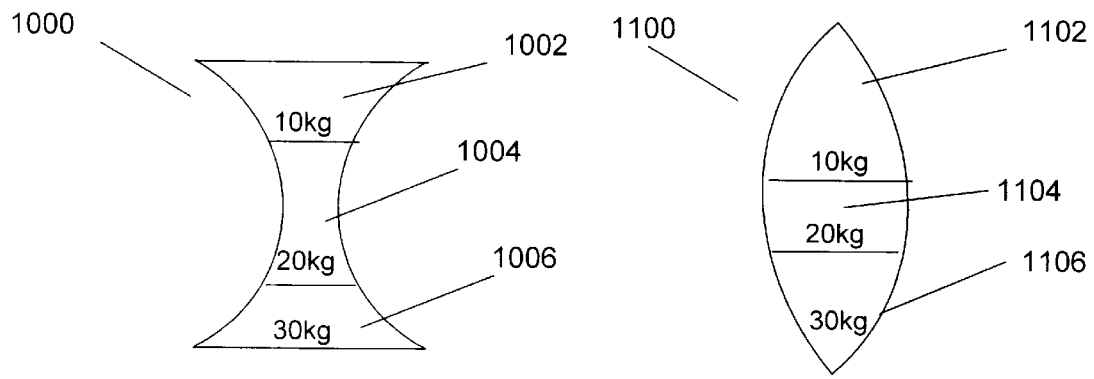
FIG. 10 is an illustration in simplified form of another container made according to the present invention.
FIG. 11 is an illustration in simplified form of another container made according to the present invention.

FIG. 8 illustrates, in simplified form, a container 800 of the present invention having a parabolic shape and including non-volumetric measuring indicia 802 and 804. FIG. 9 illustrates, in simplified form container 900 of the present invention having another shape and including non-volumetric measuring indicia 902 and 904. FIG. 10 illustrates, in simplified form container 1000 of the present invention having another shape and including non-volumetric measuring indicia 1002, 1004 and 1006. FIG. 11 illustrates, in simplified form container 1100 of the present invention having another shape and including non-volumetric measuring indicia 1102, 1104, and 1106.

Figure 12:
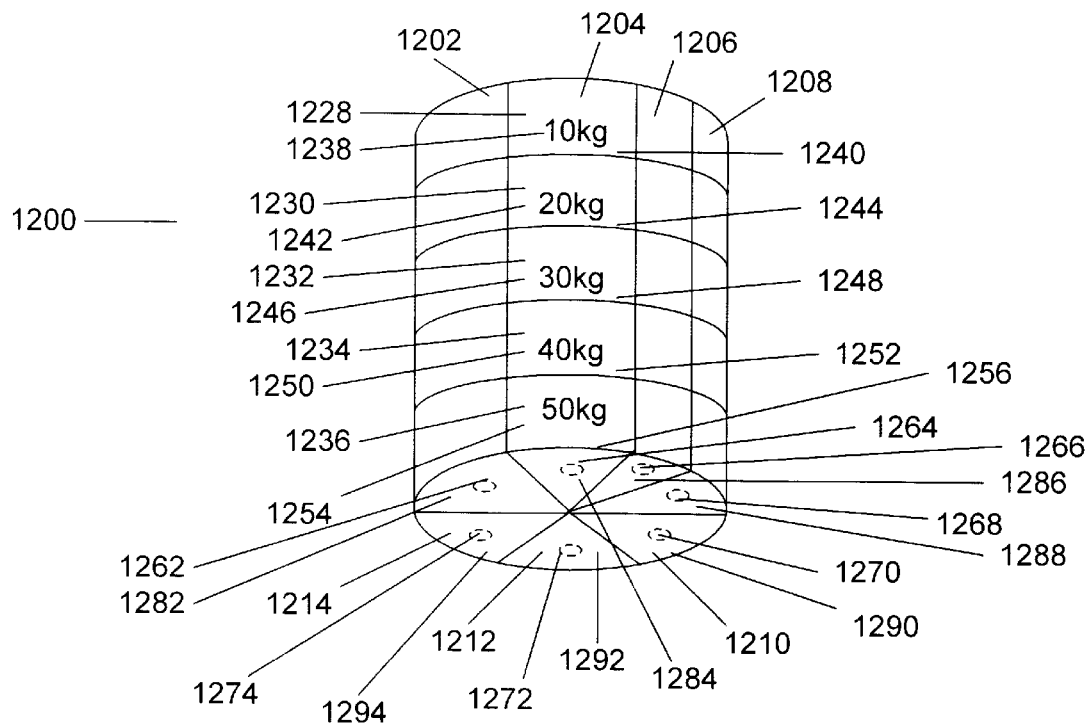
FIG. 12 is an illustration in simplified form of another container made according to the present invention.

FIG. 12 illustrates a multi-chamber container 1200 of the present invention having a cylindrical shape. Multi-chamber container 1200 includes seven sub-containers or chambers 1202, 1204, 1206, 1208, 1210, 1212, and 1214 for seven different liquid medications (not shown). Each of chambers 1202, 1204, 1206, 1208, 1210, 1212, and 1214 may be a different size, because the dosage amounts of each of the liquid medications (not shown) may be different for an individual of a given weight. On the outside of multi-chamber container 1200 are non-volumetric measuring indicia 1228, 1230, 1232, 1234 and 1236 that correspond to dosages for the liquid medications (not shown) in each of chambers 1202, 1204, 1206, and 1208 based on an individual's weight. Non-volumetric measuring indicia 1228 comprises characters 1238 and a line 1240. Non-volumetric measuring indicia 1228 corresponds to the dosages for an individual weighing 10 kg. Non-volumetric measuring indicia 1230 comprises characters 1242 and a line 1244. Non-volumetric measuring indicia 1230 corresponds to the dosages for an individual weighing 20 kg. Non-volumetric measuring indicia 1232 comprises characters 1246, and a line 1248. Non-volumetric measuring indicia 1232 corresponds to the dosages for an individual weighing 30 kg. Non-volumetric measuring indicia 1234 comprises characters 1250 and a line 1252. Non-volumetric measuring indicia 1234 corresponds to the dosages for an individual weighing 40 kg. Non-volumetric measuring indicia 1236 comprises characters 1254 and a line 1256. Non-volumetric measuring indicia 1236 corresponds to the dosages for an individual weighing 50 kg.

In use, a syringe or other withdrawal device (not shown) is inserted into multi-chamber container 1200 through sealed openings 1262, 1264, 1266, 1268, 1270, 1272, and 1274 to withdraw the appropriate amount of one or more of the seven liquid medications in chambers 1202, 1204, 1206, 1208, 1210, 1212, and 1214, For example, to withdraw the proper dosages for an individual weighing 10 kg, sufficient liquid medications are drawn into a syringe (not shown) to lower the level of liquid in one or more of chambers of 1202, 1204, 1206, 1208, 1210, 1212, and 1214 to the level of secondary non-volumetric measuring indicia 1228. Openings 1262, 1264, 1266, 1268, 1270, 1272, and 1274 are covered and sealed by seals 1282, 1284, 1286, 1288, 1290, 292, and 1294, respectively. Suitable sealing materials for seals 1282, 1284, 1286. 288, 1290, 1292, and 1294 include: plastic strips, aluminum foil, pieces of tape, etc. Before openings 1262, 1264. 1266, 1268, 1270, 1272, and 1274 are sealed, liquid medications may be poured into chambers 1202, 1204, 1206, 1208, 1210, 1212, and 1214 through openings 1262, 1264, 1266, 1268, 1270, 1272, and 1274, respectively. Depending on the medical needs of a particular individual, one, some of or all of the liquid medications in chambers 1202, 1204, 1206, 1208, 1210, 1212, and 1214 may be administered to the individual.

Figure 13:
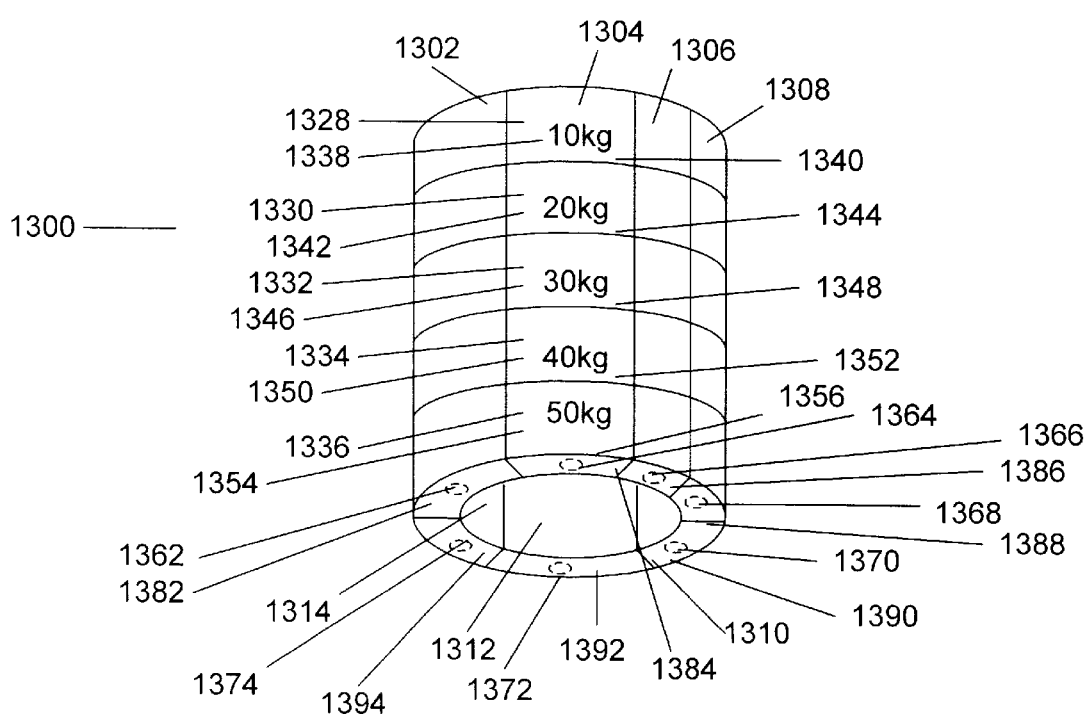
FIG. 13 is an illustration in simplified form of another container made according to the present invention.

FIG. 13 illustrates a multi-chamber container 1300 of the present invention having a hollow cylindrical shape. Multi-chamber container 1300 includes seven sub-containers or chambers 1302, 1304, 1306, 1308, 1310, 1312, and 1314 for seven different liquid medications (not shown). Each of chambers 1302, 1304. 1306, 1308, 1310, 1312, and 1314 may be a different size, because the dosage amounts of each of the liquid medications (not shown) may be different for an individual of a given weight. On the outside of multi-chamber container 1300 are non-volumetric measuring indicia 1328, 1330, 1332, 1334 and 1336 that correspond to dosages for the liquid medications (not shown) in each of chambers 1302, 1304, 1306, and 1308 based on an individual's weight. Non-volumetric measuring indicia 1328 comprises characters 1338 and a line 1340. Non-volumetric measuring indicia 1328 corresponds to the dosages for an individual weighing 10 kg. Non-volumetric measuring indicia 1330 comprises characters 1342 and a line 1344. Non-volumetric measuring indicia 1330 corresponds to the dosages for an individual weighing 20 kg. Non-volumetric measuring indicia 1332 comprises characters 1346, and a line 1348. Non-volumetric measuring indicia 1332 corresponds to the dosages for an individual weighing 30 kg. Non-volumetric measuring indicia 1334 comprises characters 1350 and a line 1352. Non-volumetric measuring indicia 1334 corresponds to the dosages for an individual weighing 40 kg. Non-volumetric measuring indicia 1336 comprises characters 1354 and a line 1356. Non-volumetric measuring indicia 1336 corresponds to the dosages for an individual weighing 50 kg.

In use, a syringe or other withdrawal device (not shown) may inserted into multi-chamber container 1300 through sealed openings 1362, 1364, 1366, 1368, 1370, 1372, and 1374 to withdraw the appropriate amount of one or more of the seven liquid medications in chambers 1302, 1304, 1306. 1308, 1310, 1312, and 1314, respectively. For example, to withdraw the proper dosages for an individual weighing 10 kg, one or more of the liquid medications are drawn into a syringe (not shown) to lower the level of liquid in one or more of chambers 1302, 1304, 1306, 1308, 1310, 1312, and 1314 to the level of secondary non-volumetric measuring indicia 1328. Openings 1362, 1364, 1366, 1368, 1370, 1372, and 1374 are covered and sealed by seals 1382, 1384, 1386, 1388, 1390, 1392, and 1394, respectively. Suitable sealing materials for seals 1382, 1384, 1386, 1388, 1390, 1392, and 1394 include: plastic strips, aluminum foil, pieces of tape, etc. Before 1362, 1364, 1366. 1368, 1370, 1372 and 1374 are sealed, liquid medications may be poured, or injected into chambers 1302, 1304. 1306, 1308, 1310, 1312, and 1314 through openings 1362, 1364, 1366, 1368, 1370, 1372, and 1374, respectively. Depending on the medical needs of a particular individual, one, some of or all of the liquid medications in chambers 1302, 1304, 1306, 1308, 1310, 1312, and 1314 may be administered to the individual.

Figures 14A, 15A:
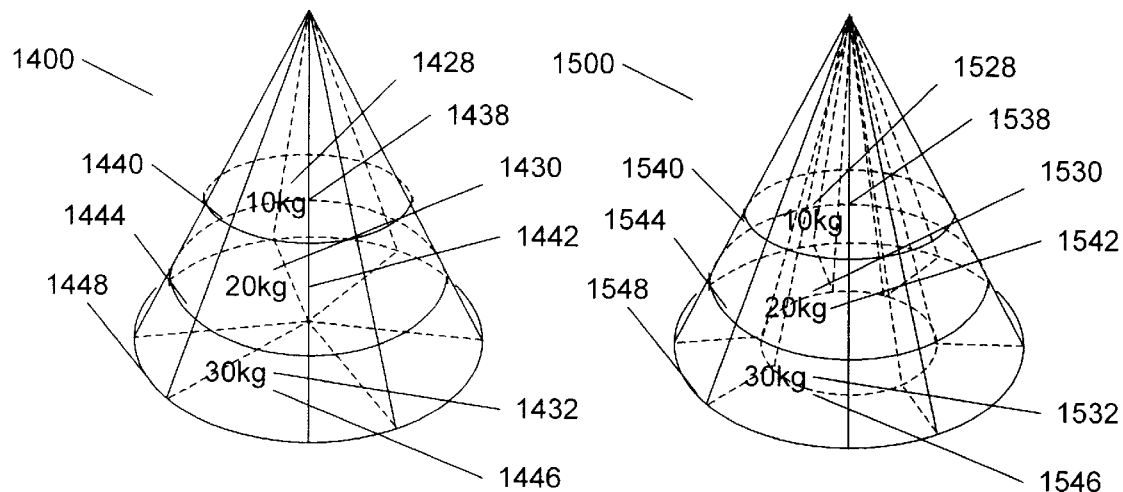
FIG. 14A is an illustration in simplified form of another container made according to the present invention.
FIG. 15A is an illustration in simplified form of another container made according to the present invention.
Figures 14B, 15B:
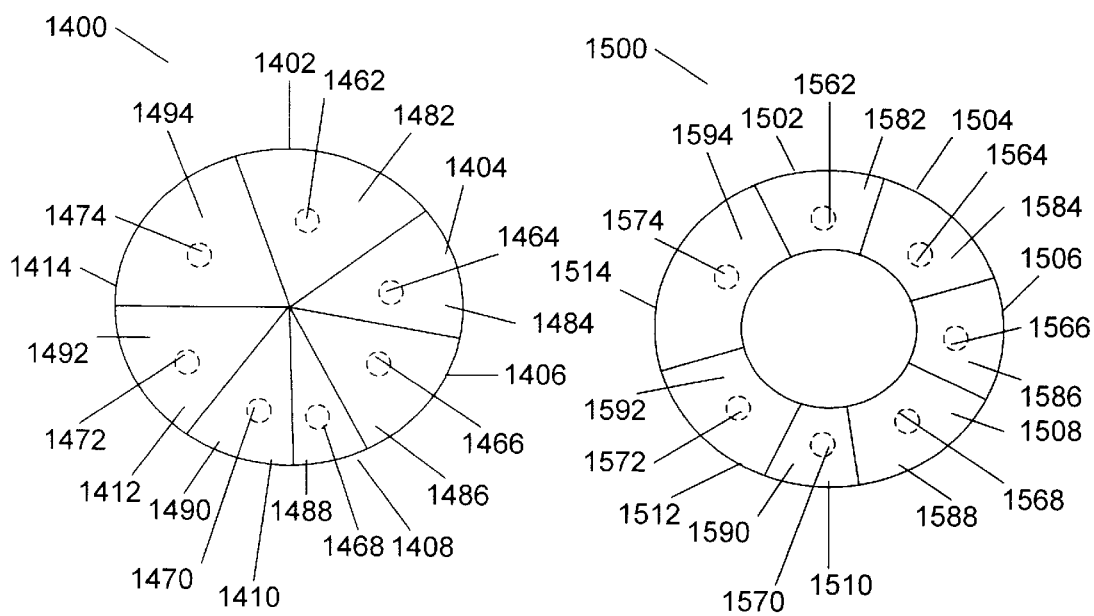
FIG. 14B is a bottom view of the container of FIG. 14A.
FIG. 15B is a bottom view of the FIG. of 15A.

FIGS. 14A and 14B illustrate a multi-chamber container 1400 of the present invention that is conical in shape. Multi-chamber container 1400 includes seven sub-containers or chambers 1402, 1404, 1406, 1408, 1410, 1412, and 1414 for seven different liquid medications (not shown). Each of chambers 1402, 1404, 1406, 1408, 1410, 1412, and 1414 may be a different size, because the dosage amounts of each of the liquid medications (not shown) may be different for an individual of a given weight. On the outside of multi-chamber container 1400 are non-volumetric measuring indicia 1428, 1430, and 1432 that correspond to dosages for the liquid medications (not shown) in each of chambers 1402, 1404, 1406, and 1408 based on an individual's weight. Non-volumetric measuring indicia 1428 comprises characters 1438 and a line 1440. Non-volumetric measuring indicia 1428 corresponds to the dosages for an individual weighing 10 kg. Non-volumetric measuring indicia 1430 comprises characters 1442 and a line 1444. Non-volumetric measuring indicia 1430 corresponds to the dosages for an individual weighing 20 kg. Non-volumetric measuring indicia 1432 comprises characters 1446, and a line 1448. Non-volumetric measuring indicia 1430 corresponds to the dosages for an individual weighing 30 kg.

In use, a syringe or other withdrawal device (not shown) may be inserted into multi-chamber container 1400 through sealed openings 1462, 1464, 1466, 1468, 1470, 1472, and 1474 to withdraw the appropriate amount of one or more of the seven liquid medications in chambers 1402, 1404, 1406, 1408, 1410, 1412, and 1414, respectively. For example, to withdraw the proper dosages for an individual weighing 10 kg, sufficient liquid medications are drawn into a syringe (not shown) to lower the level of liquid in any of chambers 1402, 1404, 1406, 1408, 1410, 1412, and 1414 to the level of non-volumetric measuring indicia 1428. Openings 1462, 1464, 1466, 1468, 1470, 1472, and 1474 are covered and sealed by seals 1482, 1484, 1486, 1488, 1490, 1492, and 1494, respectively. Suitable sealing materials for seals 1482, 1484, 1486, 1488, 1490, 1492, and 1494 include: plastic strips, aluminum foil, pieces of tape, etc. Before 1462, 1464, 1466, 1468, 1470, 1472, and 1474 are sealed, liquid medications may be poured, or injected into chambers 1402, 1404, 1406, 1408, 1410, 1412, and 1414 through openings 1462,. 1464, 1466, 1468, 1470, 1472, and 1474, respectively. Depending on the medical needs of a particular individual, one, some of or all of the liquid medications in chambers 1402, 1404, 1406, 1408, 1410, 1412, and 1414 may be administered to the individual.

FIGS. 15A and 15B illustrate a multi-chamber container 1500 of the present invention that is conical in shape. Multi-chamber container 1500 includes seven sub-containers or chambers 1502, 1504, 1506, 1508, 1510, 1512, and 1514 for seven different liquid medications (not shown). Each of chambers 1502, 1504, 1506, 1508, 1510, 1512, and 1514 may be a different size, because the dosage amounts of each of the liquid medications (not shown) may be different for an individual of a given weight. On the outside of multi-chamber container 1500 are non-volumetric measuring indicia 1528, 1530, and 1532 that correspond to dosages for the liquid medications (not shown) in each of chambers 1502, 1504, 1506, and 1508 based on an individual's weight.

Non-volumetric measuring indicia 1528 comprises characters 1538 and a line 1540. Non-volumetric measuring indicia 1528 corresponds to the dosages for an individual weighing 10 kg. Non-volumetric measuring indicia 1530 comprises characters 1542 and a line 1544. Non-volumetric measuring indicia 1530 corresponds to the dosages for an individual weighing 20 kg. Non-volumetric measuring indicia 1532 comprises characters 1546, and a line 1548. Non-volumetric measuring indicia 1530 corresponds to the dosages for an individual weighing 30 kg.

In use, a syringe or other withdrawal device (not shown) may be inserted into multi-chamber container 1500 through sealed openings 1562, 1564, 1566, 1568, 1570, 1572, and 1574 to withdraw the appropriate amount of each of the seven liquid medications in chambers 1502, 1504, 1506,. 1508, 1510, 1512, and 1514, respectively. For example, to withdraw the proper dosages for an individual weighing 10 kg, sufficient liquid medications are drawn into a syringe (not shown) to lower the level of liquid in one or more of chambers 1502, 1504, 1506, 1508, 1510, 1512, and 1514 to the level of non-volumetric measuring indicia 1528. Openings 1562, 1564, 1566, 1568, 1570, 1572, and 1574 are covered and sealed by seals 1582, 1584, 1586, 1588, 1590, 1592, and 1594, respectively. Suitable sealing materials for seals 1582, 1584, 1586, 1588, 1590, 1592, and 1594 include: plastic strips, aluminum foil, pieces of tape, etc. Before openings 1562, 1564, 1566, 1568, 1570, 1572, and 1574 are sealed, liquid medications may be poured, or injected into chambers 1502, 1504, 1506, 1508, 1510, 1512, and 1514 through openings 1562, 1564, 1566, 1568, 1570, 1572, and 1574, respectively. Depending on the medical needs of a particular individual, one, some of or all of the liquid medications in chambers 1502, 1504, 1506, 1508, 1510, 1512, and 1514 may be administered to the individual.

Figure 16:
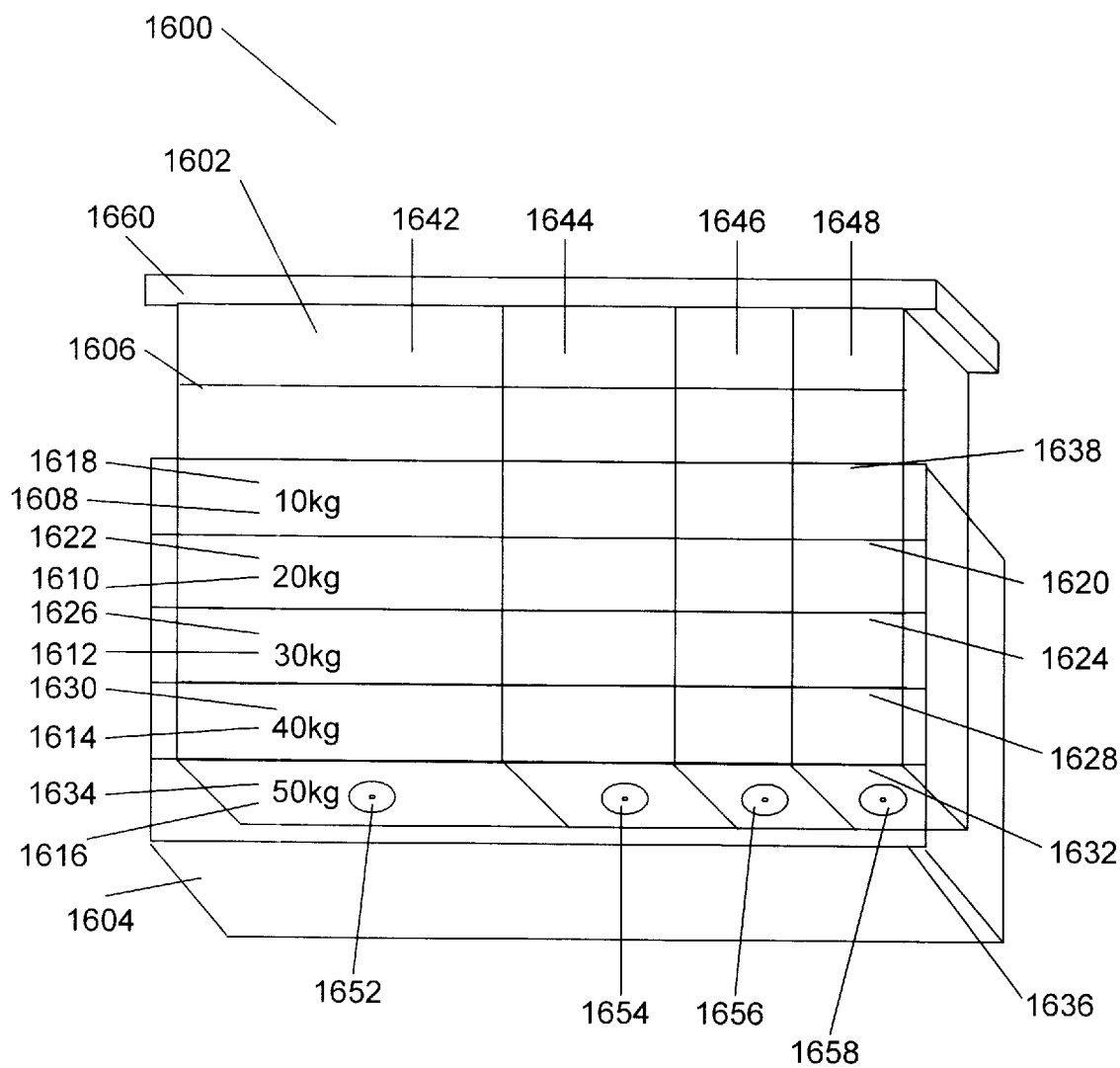
FIG. 16 is an illustration of another container made according to the present invention.

FIG. 16 illustrates a container 1600 of the present invention that includes a body portion 1602 and a transparent sleeve 1604. Body portion 1602 includes reference markings 1606. Transparent sleeve 1604 includes non-volumetric measuring indicia 1608, 1610, 1612, 1614, and 1616. Non-volumetric measuring indicia 1608 comprises characters 1618 and line 1620. Non-volumetric measuring indicia 1610 comprises characters 1622 and line 1624. Non-volumetric measuring indicia 1612 comprises characters 1626 and line 1628. Non-volumetric measuring indicia 1614 comprises characters 1630 and line 1632. Non-volumetric measuring indicia 1616 comprises characters 1634 and line 1636. Transparent sleeve 1604 can be used to recalibrate container 1600 by sliding transparent sleeve 1604 so that a top line 1638 of transparent sleeve 1604 is even with the current level of liquid (not shown for simplicity) in container 1600. Transparent sleeve 1604 may be held in place on container 1600 by gripping transparent sleeve 1604 against container 1600.

Container 1600 includes four sub-containers or chambers 1642, 1644, 1646, and 1648 for four different liquid medications (not shown). Each of chambers 1642, 1644, 1646, and 1648 may be a different size, because the dosage amounts of each of the liquid medications (not shown) may be different for an individual of a given weight. In use, a syringe or other withdrawal device (not shown) may be inserted into multi-chamber container 1600 through resealable openings 1652, 1654, 1656 and 1658 to withdraw the appropriate amount of each of the four liquid medications in chambers 1642, 1644, 1646, and 1648, respectively. The appropriate amounts of each of the liquid medications (not shown) filling chambers 1642, 1644, 1646, and 1648, to be administered to an individual of a particular weight is indicated by non-volumetric measuring indicia 1608, 1610, 1612 and 1614 on transparent sleeve 1604. Resealable openings 1652, 1654, 1656, and 1658 are conventional resealable openings or valve devices made of rubber, plastic, cork etc. that are conventionally used to allow a liquid in a container to be withdrawn by a syringe or other withdrawal device. Depending on the medical needs of a particular individual, one, some of or all of the liquid medications in chambers 1642, 1644, 1646, and 1648 may be administered to the individual.

Chambers 1642, 1644, 1646, and 1648 may be filled with liquid medications (not shown) by removing a cap 1660 that snap fits onto container 1600, or by injecting through resealable openings 1652, 1654, 1656, and 1658, respectively. Although only one type of cap is shown in FIG. 6A, any kind of conventional cap may be used to close container 1600.

Although one particular type of recalibration device, a sleeve, including non-volumetric measuring indicia is shown in FIG. 16, various types of recalibration devices may be used to recalibrate the container of the present invention. For example, a transparent card or sheet including non-volumetric measuring indicia may be held against the container of the present invention to recalibrate the container.

The container of the present invention is preferably made of a transparent or translucent material such as plastic, Plexiglas, or glass. Although only a few types of shapes are illustrated above for the container of the present invention, the container of the present invention may have a wide variety of sizes and shapes depending on how the container is used for a particular application. Similarly, any portion of the container may be color coded to aid in visualizing horizontal lines indicating particular weights, heights, etc.

Also, different chambers of the container may be color coded to indicate particular drugs or drugs for particular applications. For example, cardiac drugs could be located in blue colored chambers, rapid sequence intubation drugs in green colored chambers, antidote drugs in yellow chambers, etc.

Although particular weight and height ranges are shown for the syringes and containers of the present invention described above and shown in the drawings, various weight and height ranges may be used depending on the setting. For example, a syringe or container of the present invention may be specially made for use with infants having relatively small age or height ranges.

Although only a few types of non-volumetric measuring indicia are shown for the syringes and containers described above, the present invention encompasses any kind of non-volumetric marking that may be used on a syringe or container, such as abstract symbols; pictures of humans as: babies, children, adults; etc.

Although the container of the present invention has only been described above with respect to using a syringe to withdraw liquid, the container of the present invention may include a valve to allow for liquid to be withdrawn from the container. An example of such a valve is a conventional luer-lock that allows liquid to be withdrawn from the container into a tube or luer.

Although dosage levels generally increase linearly with respect to the weight, age, etc. of an individual to which a drug is administered, in some circumstances, the relationship may not be linear and the non-volumetric markings and intermediate marking on the syringe or container of the present invention may be located appropriately to reflect a non-linear relationship.

The present invention also encompasses the use of multiple types of indicia used simultaneously on a syringe or container. For example, for a particular medication, the weight 350 kg and 150 cm could be listed together at the same line of a syringe or container. Similarly, for liquid medications where the dosage may be different depending on whether an individual is male or female, two different weights or heights, one for a male and one for a female, may be listed together at the same line on the syringe or container.

In a typical resuscitation scenario, a patient arrives and weight is assessed based on age or using a Broselow tape that determines weight based on a patient's height. The physician evaluates the situation, chooses the optimal drug, and calculates the drug dose based on the patients' weight (mg/kg). For example, the dose of Atropine in mg based on weight is 0.02 mg/kg. For a 10 kg child, 0.2 mg would be requested. The nurse, informed of the mg dose, performs another calculation to determine the quantity of drug to administer in cubic centimeters. Atropine is dispensed as a 0.01 mg/cc concentration. Thus, the dose of Atropine in cc/kg would be 0.2 cc/kg. For a 10 kg child, 2 cc would be required.

Using the above scenario and the container of the present invention, a patient arrives, the patient's weight is assessed, and the physician chooses Atropine. The nurse inserts a needle into a container containing Atropine or the Atropine chamber of a multi-chamber container, and withdraws the drug until the liquid reaches the mark on the container corresponding to the weight of the patient. The container of the present invention allows a user to determine the amount of drug to be administered based directly on the patient's weight, eliminating the need to make the mathematical conversion from kilograms of patient weight to cubic centimeters of administered drug. Furthermore, when a multi-chamber multi-drug container of the present invention is used, the amount of each administered drug may be directly determined by just one number such as the patient's weight, height, etc. In contrast, using the current procedure to administer multiple drugs, a conversion from patient weight to milligrams and again to cubic centimeters of administered drug must be made for each and every drug, thereby providing multiple opportunities for errors to occur.

The typical scenario requires multiple mathematical calculations and allows for errors to be committed at each step.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A container comprising:
   at least one chamber;
   a plurality of non-volumetric measuring indicia on said at least one chamber; and
   an opening control device in said at least one chamber for allowing liquid contained in said at least one chamber to be withdrawn from said at least one chamber.

2. The container of claim 1, wherein said opening control device comprises a needle receiving section for being penetrated by a syringe needle.

3. The container of claim 1, wherein said opening control device comprises an opening and a covering material for sealing said opening and for being penetrated by a syringe needle.

4. The container of claim 1, wherein said plurality of non-volumetric measuring indicia comprise numeric indicia.

5. The container of claim 1, wherein said plurality of non-volumetric measuring indicia comprise a plurality of color indicia.

6. The container of claim 1, wherein said plurality of non-volumetric measuring indicia comprise a plurality of weight indicia.

7. The container of claim 1, wherein said plurality of non-volumetric measuring indicia comprise a plurality of age indicia.

8. The container of claim 1, wherein said plurality of non-volumetric measuring indicia comprise a plurality of height indicia.

9. The container of claim 1, wherein said at least one chamber has a rectangular cross-section.

10. The container of claim 1, wherein said at least one chamber is tapered.

11. The container of claim 1, wherein said at least one chamber is right-triangularly tapered.

12. The container of claim 1, wherein said at least one chamber comprises a plurality of chambers.

13. The container of claim 12, wherein said plurality of chambers comprise modular chambers.

14. The container of claim 12, wherein said plurality of chambers comprises a rectangular block of chambers.

15. The container of claim 12, wherein said plurality of chambers comprises a right-triangularly tapered block of chambers.

16. The container of claim 12, wherein said plurality of chambers comprises a solid cylinder of chambers.

17. The container of claim 12, wherein said plurality of chambers comprises a hollow cylinder of chambers.

18. The container of claim 12, wherein said plurality of chambers comprises a solid cone of chambers.

19. The container of claim 12, wherein said plurality of chambers comprises a hollow cone of chambers.

20. The container of claim 8, further comprising a recalibration means for adjusting the location of said plurality of non-volumetric measuring indicia with respect to said at least one chamber.

* * * * *